United States Patent [19]

Hutson

[11] Patent Number: 5,242,416
[45] Date of Patent: Sep. 7, 1993

[54] SHIELD ASSEMBLY FOR NEEDLE SYRINGES

[76] Inventor: Clifford L. Hutson, 4440-J Shadow Hills Cir., Santa Barbara, Calif. 93105

[21] Appl. No.: 818,804

[22] Filed: Jan. 9, 1992

[51] Int. Cl.⁵ .............................................. A61M 5/32
[52] U.S. Cl. .................................... 604/192; 604/198
[58] Field of Search ................ 604/263, 187, 198, 192

[56] References Cited

U.S. PATENT DOCUMENTS

| | | |
|---|---|---|
| 2,571,653 | 10/1951 | Bastien . |
| 3,658,061 | 4/1972 | Hall . |
| 4,356,822 | 11/1982 | Winstead-Hall . |
| 4,373,526 | 2/1983 | Kling . |
| 4,425,120 | 1/1984 | Sampson et al. . |
| 4,500,312 | 2/1985 | McFarlane . |
| 4,573,975 | 3/1986 | Frist et al. . |
| 4,573,981 | 3/1986 | McFarlane . |
| 4,631,057 | 12/1986 | Mitchell . |
| 4,664,259 | 5/1987 | Landis . |
| 4,717,386 | 1/1988 | Simmons . |
| 4,723,943 | 2/1988 | Spencer . |
| 4,737,144 | 4/1988 | Choksi ............................ 604/198 |
| 4,737,149 | 4/1988 | Gillilan . |
| 4,738,663 | 4/1988 | Bogan . |
| 4,747,837 | 5/1988 | Hauck . |
| 4,781,697 | 11/1988 | Slaughter . |
| 4,820,277 | 4/1989 | Norelli . |
| 4,840,618 | 6/1989 | Marvel . |
| 4,850,976 | 7/1989 | Heinrich et al. . |
| 4,886,503 | 12/1989 | Miller . |
| 4,897,083 | 1/1990 | Martell . |
| 4,898,589 | 2/1990 | Dolgin et al. . |
| 4,900,309 | 2/1990 | Netherton et al. . |
| 4,911,693 | 3/1990 | Paris .................................... 604/192 |
| 4,919,656 | 4/1990 | Bracker et al. . |
| 4,923,446 | 5/1990 | Page et al. . |
| 4,923,447 | 5/1990 | Morgan ........................... 604/263 X |
| 4,927,018 | 5/1990 | Yang et al. . |
| 4,927,416 | 5/1990 | Tomkiel .............................. 604/198 |
| 4,950,249 | 8/1990 | Jagger et al. . |
| 4,966,591 | 10/1990 | Yuen . |
| 4,976,702 | 12/1990 | Andrews et al. . |
| 4,981,476 | 1/1991 | Aichlmayr et al. . |
| 4,986,817 | 1/1991 | Code . |
| 4,998,920 | 3/1991 | Johnson . |
| 5,024,616 | 6/1991 | Ogle, II ........................... 604/198 X |

*Primary Examiner*—John D. Yasko
*Attorney, Agent, or Firm*—John A. Bucher

[57] ABSTRACT

Five embodiments of a shield assembly for a syringe having a plunger barrel and a mounting at the other end of the syringe for receiving a needle hub, an inner sheath adapted for being secured to the syringe, an outer cylindrical sheath in telescoping relation on the inner sheath and movable between a retracted position and extended position, and locking elements formed on the two sheaths for locking them in extended and/or retracted relation, the locking elements being releasable by relative rotation of the sheaths. The various embodiments include an additional intermediate sheath nested between the inner and outer sheaths with the locking elements functioning through the three sheaths, guide elements for maintaining alignment of the locking elements, a spiral track for effecting relative rotation of adjacent sheaths.

13 Claims, 5 Drawing Sheets

SHIELD ASSEMBLY FOR NEEDLE SYRINGES

FIELD OF THE INVENTION

The present invention relates to syringes of a type having a needle and more particularly to a shield assembly for such syringes.

BACKGROUND OF THE INVENTION

Needles syringes or hypodermic syringes as they are more commonly termed are commonly employed for injecting fluids into both humans and animals. Such hypodermic syringes commonly include a barrel or body for containing the fluid to be injected. A plunger is usually operable at one end of the barrel for forcing the fluid from the barrel through a needle which is commonly mounted by means of a needle hub at the other end of the barrel. The preceding description of a hypodermic syringe is set forth herein only as an example and is not intended to be limiting in terms of the present invention.

Syringes of the type described above are widely used by health professionals such as doctors, nurses, lab technicians, hospital staff and others providing treatment particularly for human patients.

However, regardless of the particular application for the syringe, it has become important to protect the health professionals and others during the manipulation of hypodermic syringes, intravenous needles and the like, for example, to administer medication and/or to aspirate blood or other body fluids. Such protection is particularly essential after the syringe has been used either for injection or aspiration in order to assure that the needle does not penetrate any body portion of the operator. So-called "needle sticks" have proven to be particularly serious where the syringe has been employed on a patient having an infectious disease.

In such situations, the syringe has been known to slip from an operator's hand with its possibly contaminated needle penetrating part of the operator's body such as a leg, foot or hand. The most common form of "needle stick" injury is in recapping the needle with a standard cap after use of the syringe. Various shield assemblies have been employed in the past for minimizing or eliminating such accidents. Usually, it is necessary for the operator to position the shield or allow the shield to automatically assume a position for shielding the needle from subsequent contact. Typical prior art examples of such shield devices are discussed in greater detail below.

For example, U.S. Pat. No. 4,631,057, issued Dec. 23, 1986 to Mitchell disclosed such an apparatus having two relatively movable cylinders for engaging a syringe barrel to provide such a shielding function. U.S. Pat. No. 4,897,083, issued Jan. 30, 1990 to Martell disclosed yet another syringe needle guard including multiple cylinders telescopically arranged for extension and retraction to accomplish a similar purpose.

U.S. Pat. No. 3,658,061, issued Apr. 25, 1972 to Hall and U.S. Pat. No. 4,664,259, issued May 12, 1987 to Landis both provided needle guard units including hinged shield components or covers capable of being swung into protective relation with a needle.

U.S. Pat. No. 4,927,018 issued May 22, 1990 to Yang, et al. disclosed yet another needle assembly and cylindrical cover housing which is believed to be representative of a number of similar prior art references wherein a syringe or a portion of the syringe such as a needle hub requires modification for use of the syringe with the shield assembly.

U.S. Pat. No. 4,976,702, issued Dec. 11, 1990 to Andrews, et al. also disclosed a syringe needle guard or shield adapted for mounting on a hub by which the needle was secured to a syringe. U.S. Pat. No. 4,373,526, issued Feb. 15, 1983 to Kling disclosed a sheath assembly for an injection wherein the sheath was configured to apply pressure to the skin during injection for one or more desired purposes.

Additional references disclosing such devices include, for example, U.S. Pat. No. 4,356,822, issued Nov. 2, 1982 to Winstead-Hall; U.S. Pat. No. 4,738,663, issued Apr. 19, 1988 to Bogan and U.S. Pat. No. 4,900,309, issued Feb. 13, 1990 to Netherton, et al. It is noted once again that all or most of the above references are representative of additional prior art relating to such protective shields or devices. In any event, these devices have been found generally satisfactory for their intended purpose. At the same time, there has been found an obvious need for further improvements in such protective devices, for example, either to simplify or improve use of the syringes while protecting those handling the syringes or capable of coming into contact with them.

SUMMARY OF THE INVENTION

Accordingly, it is an object of the present invention to provide an improved shield assembly for such syringes to provide protection against accidental contact of the needles, particularly after use.

It is particularly noted that many hypodermic syringes presently used in medical offices, hospitals and the like are of a disposable type. They may be made in different standard sizes, for example, of 3 cc, 5 cc, 10 cc capacities and even larger for certain applications.

Both the syringe and needle are commonly disposable. In addition, the needle may be secured and packaged with the syringe as a sterilized unit. Larger size syringes commonly have the needles packaged separately.

In any event, it is another object of the invention to particularly adapted the shield assembly for use with such existing syringes. With the syringe and/or needle being disposable, the shield assembly may be employed as a protective unit during disposal. On the other hand, it is also possible to use the shield assembly with the syringe and then dispose of the needle and/or syringe while retrieving and sterilizing the shield assembly for subsequent use.

It is also an object of the invention to provide a shield assembly for a separate or pre-existing syringe, the shield assembly including an inner cylindrical sheath for receiving and engaging a portion of the syringe, an outer cylindrical sheath movable on the inner sheath between a first position shielding a needle or needle assembly of the syringe and a second position exposing the needle or neddle assembly for normal operation of the syringe, and locking means for securing the outer sheath in a selected position on the inner sheath.

It is a more specific object of the invention to provide a shield assembly for a syringe comprising an inner sheath secured to a portion of the syringe, an outer cylindrical sheath arranged in telescopic relation with the inner cylindrical sheath and movable between a retracted position and an extended position, and locking means formed on both of the sheaths and arranged for operative interaction with each other to lock the outer sheath in its extended position for shielding the needle, the locking means being releasable by relative rotation of the sheaths to permit retraction of the outer sheath when desired.

In the above combination, means are provided for capping the outer sheath in its extended position. The inner sheath may be configured for mounting either on the syringe barrel or on the needle hub, for example. An intermediate sheath may also be arranged in nested relation between the inner and outer sheaths, the locking means including means for respective interaction between the inner and intermediate sheaths and also between the intermediate and outer sheaths.

It is also contemplated within the above combination that a spiral track may be formed on one of the sheaths with projecting means on an adjacent sheath for capturing the spiral track in order to regulate retraction and extension therebetween by relative rotation of the sheaths. Preferably, additional means are provided for preventing accidental separation of the adjacent sheaths.

It is a further related object of the invention to provide a shield assembly as initially defined above together with guide means formed on the adjacent sheaths and arranged for operative interaction to maintain the lock means in alignment with each other.

In such an embodiment, the locking means preferably comprise resilient tabs extending tangentially from a relatively inner sheath for engagement with an opening formed in a relatively outer sheath. Cutout tabs facing in opposite circumferential directions are preferably provided for interaction with an opening in the outer sheath to provide locking means in both the relatively retracted and extended positions for the sheaths. With such an arrangement, the adjacent sheaths are rotated in opposite directions for releasing them from locking engagement.

It is a still further object of the invention to provide a shield assembly as described above with one or more spring means arranged between adjacent sheaths for urging the sheaths into relative extended relation.

It is also a further object of the invention to provide a shield assembly as described above and including hinge means permitting hinged movement of a portion of at least one sheath for exposing the needle or needle assembly and thereby permitting normal operation of the syringe.

Additional objects and advantages of the invention are described below with reference to the accompanying drawings.

BRIEF DESCRIPTION OF THE DRAWINGS

FIG. 8 is a view taken along section line VIII—VIII in FIG. 7.

FIG. 11 is an axially sectioned side view of a second embodiment of a shield assembly constructed according to the present invention for use on a hypodermic syringe and the like.

FIG. 12 is a longitudinal side view of an inner cylindrical sheath in the shield assembly of FIG. 11.

FIG. 13 is an end view of the inner sheath taken from the right end of the sheath as illustrated in FIG. 12.

FIG. 14 is a view taken along section line XIV—XIV of FIG. 12.

FIG. 16 is a view taken along section line XVI—XVI in FIG. 15.

FIG. 18 is a view taken along section line XVIII—XVIII of FIG. 17.

DESCRIPTION OF THE PREFERRED EMBODIMENTS

As indicated above, five embodiments of shield assemblies constructed according to the present invention are illustrated in the drawings. Before describing each of the embodiments in detail, principal features of each of the five embodiments are briefly summarized below.

Figure 1:
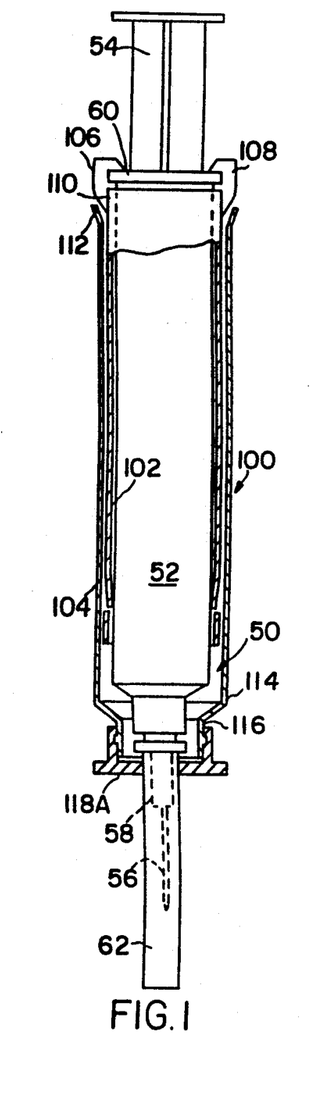
FIG. 1 is an axially sectioned side view of one embodiment of a shield assembly according to the present invention mounted upon a hypodermic syringe.

A hypodermic syringe of a type contemplated for use with all five embodiments of the invention is generally indicated at 50 in FIG. 1 for the first embodiment. Where alternate components are provided on the hypodermic syringe, they are represented by primed numerals in the other embodiments.

In the first embodiment of the invention as illustrated in FIGS. 1-10, the shield assembly is generally indicated at 100 and includes inner and outer cylindrical sheaths 102 and 104 described in greater detail below.

Figures 11, 12, 13, 14, 16, 18:
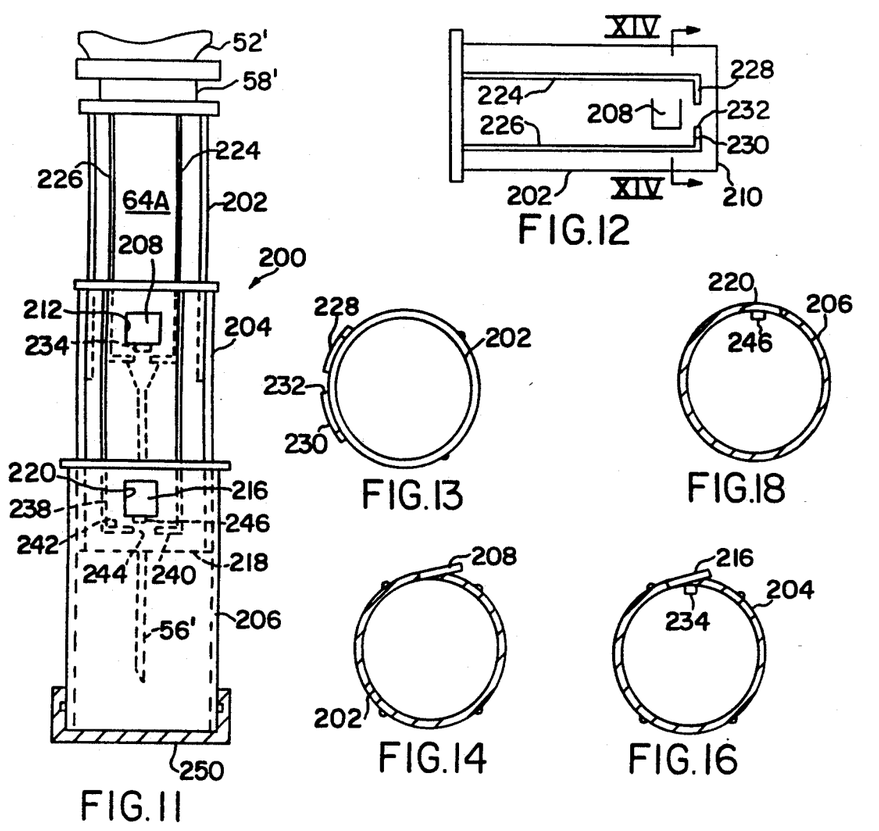
Figure 15:
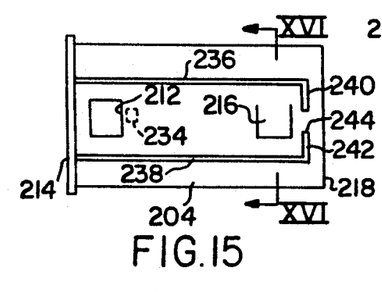
FIG. 15 is a longitudinal side view of an intermediate sheath in the shield assembly of FIG. 11.
Figure 19:
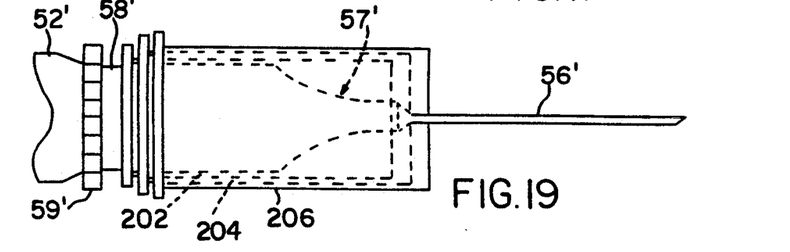
FIG. 19 is a side view of the shield assembly of FIG. 11 with the sheaths relatively retracted in nested relation to expose the hypodermic needle.

In the second embodiment illustrated in FIGS. 11-19, the shield assembly is generally indicated at 200 and includes an inner cylindrical sheath indicated at 202, an intermediate cylindrical sheath indicated at 204 and an outer cylindrical sheath indicated at 206. Here again, the inner, intermediate and outer sheaths 202-206 are arranged in telescoping relation so that they can be moved between relatively retracted and relatively extended positions to either expose a hypodermic needle as illustrated in FIG. 19 or to enclose the needle as illustrated in FIG. 11.

A third embodiment of a shield assembly constructed according to the present invention is generally indicated at 300 in FIGS. 20-29. The shield assembly 300 also includes inner, intermediate and outer cylindrical sheaths respectively indicated at 302, 304 and 306. The sheaths 302-306 are nested and adapted for retraction and extension in generally the same manner as the sheaths in the shield assembly 200 of FIGS. 11-19, as described above.

A fourth embodiment of a shield assembly constructed according to the present invention is generally indicated at 400 in FIGS. 30-36. The shield assembly 400 includes inner, intermediate and outer cylindrical sheaths respectively indicated at 402, 404 and 406. The sheaths 402-406 are nested and adapted for retraction and extension also in generally the same manner described above for the other embodiments. However, the shield assembly 400 is also provided with separate spring means 408 and 410 arranged respectively for interaction between the inner and intermediate sheaths and between the intermediate and outer sheaths for urging the three sheaths of the shield assembly 400 into the extended condition illustrated in FIG. 30.

A fifth embodiment of a shield assembly constructed according to the present invention is generally indicated at 500 in FIGS. 37-42. The shield assembly 500 includes inner and outer cylindrical sheaths 502 and 504. The inner sheath 502 is formed in two portions 502A and 502B which are interconnected by a flexible hinge 506. The inner and outer sheaths are constructed to permit movement of the inner sheath portion 502B and the outer sheath 504 between a first position shielding the needle and a second or hinged position to expose the needle and permit normal operation of the syringe.

It is to be noted that certain features of each embodiment could be employed in one or more of the other embodiments. For example, although the first embodiment or shield assembly 100 of FIGS. 1-10 is described only with inner and outer sheaths, it could also be provided with an intermediate cylindrical sheath (not shown). Similarly, although the two shield assemblies 200 and 300 of FIGS. 11-19 and 20-29 respectively are illustrated with inner, intermediate and outer cylindrical sheaths, it is to be understood that those shield assemblies could also be constructed with only two sheaths.

Further variations or modifications in the various shield assembly embodiments are noted in the following detailed description.

Referring now to FIGS. 1-10, and more particularly to FIG. 1, the hypodermic syringe 50 is not a part of the invention but is illustrated only as an example of hypodermic syringes, intravenous devices and the like equipped with a needle to be protected by the shield assembly 100.

Various components of the shield assembly 100 are preferably formed from plastic, more preferably from a plastic which is clear or translucent in order to permit a user to observe indices and the like printed on the syringe.

The syringe 50 includes an elongated barrel 52, typically of a type having graduated indices (not shown) printed thereon to permit a user to monitor amounts of liquid remaining in the syringe or expelled therefrom. The barrel 52 is equipped with a conventional plunger 54 at one end of the barrel, the plunger 54 being conventionally movable by a user for causing liquid to be expelled from the barrel through a needle 56 secured to an opposite end of the barrel 52, for example, by means of a needle hub 58 having a flange 59.

Different needle devices are contemplated by the present invention and are commonly employed with syringes such as that indicated at 50. The needle device generally illustrated in FIG. 1 is one common type manufactured for example by Beckton-Dickenson under the trade name SLIP-ON TIP. Another type of needle device is illustrated for example in FIGS. 19 and 29 as described in greater detail below and is manufactured for example by Becton-Dickenson under the trade name LUER-LOC TIP.

In any event, it is to be understood that a wide variety of such needle devices are contemplated by the present invention. The various embodiments of shield assemblies described below are adapted for use generally with any of the different types of needle devices.

The syringe 50 also has a flange 60 formed at the first end of the barrel 52 adjacent the plunger 54. The flange 60 is commonly employed by users to facilitate manipulation of the syringe 50 while operating the plunger 54.

As noted above, the shield assembly 100 includes an inner cylindrical sheath 102 and an outer cylindrical sheath 104.

The inner sheath 102 is preferably sized to fit over or receive the barrel 52 of the syringe 50. At the same time, the inner cylindrical sheath 102 has diametrically opposed flexible clips 106 and 108 extending axially from the one end 110 of the barrel for snapping into engagement with the flange 60 and securing the inner cylindrical sheath 102 and accordingly the remaining components of the shield assembly 100 in place upon the syringe 50. Otherwise, the inner cylindrical sheath 102 is generally of the same length as the syringe barrel 52.

Figure 2:
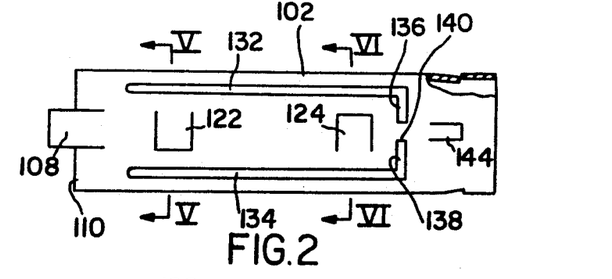
FIG. 2 is a longitudinal side view of an inner sheath of the shield assembly.
Figure 3:
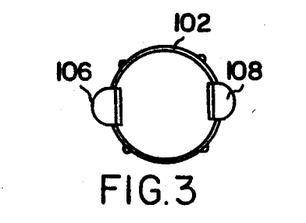
FIG. 3 is a view taken from the left end of the inner sheath as shown in FIG. 2.
Figure 4:
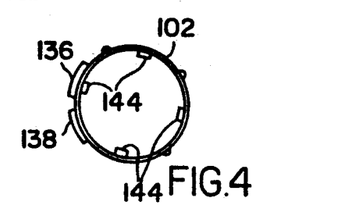
FIG. 4 is a view taken from the right end of the inner sheath as illustrated in FIG. 2.
Figure 5:
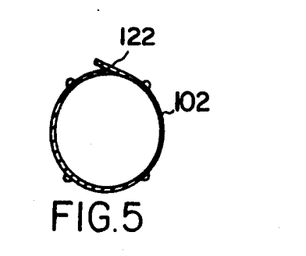
FIGS. 5 and 6 are views taken respectively along section lines V—V and VI—VI in FIG. 2.
Figure 6:
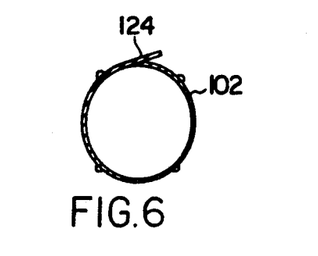

The outer cylindrical sheath 104 is formed with an inside diameter just larger than the outside diameter of the inner cylindrical sheath 102 so that the outer sheath 104 can be arranged in telescoping or nested relation with respect to the inner sheath 102. It is also to be noted that the inner sheath 102 is formed with ridges 132 and 134 as illustrated in FIG. 2 and described further below. The ridges are arranged to contact the inner diameter of the outer sheath 104. Referring also to FIG. 3, two similar elongated ridges 132 and 134 are formed on an opposite side of the inner sheath 102. Thus, the four ridges maintain slight separation between the inner and outer sheaths 102 and 104 to assure smooth telescopic interaction of the sheaths. The four ridges illustrated in FIG. 3 could possibly be replaced by three ridges to accomplish generally the same purpose.

One end 112 of the outer sheath 104 is preferably flared in order to facilitate positioning of the inner cylindrical sheath 102 within the outer sheath 104. Perhaps the most important reason for the flared end 112 is to facilitate functioning of the outer sheath when it is retracted to its fully nested position (see FIG. 1). When the outer sheath 102 is retracted, the flared end 112 engages a locking tab 122, described in greater detail below and illustrated in FIG. 2. Engagement of the tab 122 with the curved surface of the flared end 112 causes the locking tab to be depressed so that it can readily be captured by the inside surface of the outer sheath and thereafter engage a recess 126 also described in greater detail below and illustrated in FIG. 9.

The other end 114 of the outer sheath 104 is preferably formed with a reduced diameter flange 116 adapted for receiving a cap.

Figure 9:
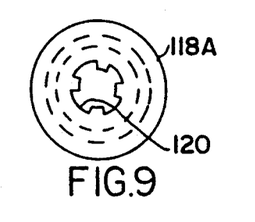
FIGS. 9 and 10 are representations of alternative caps for use on the outer cylindrical sheath in the shield assembly of FIG. 1.

In FIG. 1, a receptor cap 118A is illustrated in place upon the flange 116 and also in FIG. 9. The receptor cap 118A is formed with an axial opening 120. The receptor cap 118A permits the outer sheath 104 to be retracted upon the inner sheath 102 as illustrated in FIG. 1 with the needle 56 and a conventional needle cap 62 enclosing the otherwise exposed needle.

There are generally three ways to use the shield assembly illustrated in FIG. 1. These three different methods of use are described below.

(1) The shield assembly including the inner and outer sheaths are mounted on the syringe or the shield assembly may form part of a commercial product together with the syringe. In either case, the needle is attached as illustrated and protected by the conventional needle cap 62. With the shield assembly in place, the needle cap is removed and the syringe employed in the usual manner. Thereafter, the outer sheath of the shield assembly is extended over the needle for protection. The operator may then choose not to recap the needle or the outer sheath but to dispose of the syringe needle and shield assembly as a single unit, the outer sheath being locked in position over the needle.

(2) A solid molded cap may be placed on the extended outer sheath to protect the needle temporarily prior to additional use. For example, such a mode of operation may be employed where intermittent injections are required during an operation. It may then be disposed of with the solid cap attached or the operator may choose to cap the extended outer sheath immediately after use and then dispose of the entire assembly.

(3) A specially designed receptor cap illustrated for example at 118A in FIG. 9 may be used only if recapping of the needle with the original needle cap is required. Such a procedure could be employed for example if the shield assembly were to be saved and sterilized for re-use. In that event, the capped needle and syringe could be disposed of in the usual manner.

Lock means described immediately below are formed on both the inner and outer sheaths 102 and 104 and are arranged for operative interaction with each other in order to lock the outer cylindrical sheath 104 at least in an extended position relative to the inner sheath 102 for shielding the needle 56, preferably with the needle cap 62 removed. The locking means are further formed as described below to be releasable by relative rotation of the inner and outer cylindrical sheaths for permitting retraction of the outer sheath 104 into the position illustrated in FIG. 1 when desired.

It is to be understood that, although an intermediate sheath is not illustrated in the embodiment of FIGS. 1-10, such an intermediate sheath could be employed similarly as described below with reference to the embodiments of FIGS. 11-19 and 20-29. Accordingly, the locking means described herein are intended to be suitable for operative interaction either directly with each other or through additional locking means on such an intermediate sheath (not shown).

The locking means formed on the inner and outer sheaths 102 and 104 are preferably adapted for locking the outer sheath 104 in either an extended position as described above to shield the needle 56 or in the retracted position illustrated in FIG. 1. The locking means comprise projections 122 and 124 formed on the inner sheath 102 and a single recess or opening 126 formed on the outer sheath 104. The projections 122 and 124 are preferably formed as tabs which are integrally formed by the inner sheath 102 to be flexible and to extend generally tangentially from the inner sheath 102. As illustrated in FIG. 2, the projections or tabs 122 and 124 are preferably of a generally rectangular configuration. At the same time, the recess or opening 126 formed in the outer sheath 104 is of generally the same configuration as the projections 122 and 124 while being slightly larger than the projections in order to permit either of the projections to flex outwardly into engagement with the recess 126.

The projections or tabs 122 and 124 also extend in opposite directions from the inner sheath 102 while being in substantially axial alignment thereupon. Referring particularly again to FIG. 2, the first projection or tab 122 extends downwardly while the second projection or tab 124 extends upwardly from the inner sheath 102 as viewed therein. The flexible and generally tangential arrangement of the tabs 122 and 124 on the inner sheath 102 is illustrated in greater detail respectively in FIGS. 5 and 6.

With the outer sheath 104 positioned in nested relation upon the inner sheath 102 and retracted as illustrated in FIG. 1, the first tab 122 would then register with the recess 126 in order to lock the outer sheath 104 in its retracted position.

Figure 7:
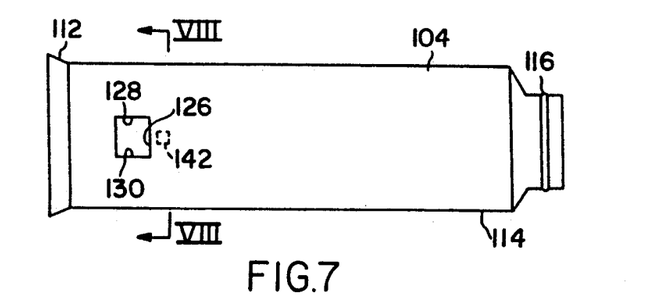
FIG. 7 is a longitudinal view of an outer cylindrical sheath in the shield assembly of FIG. 1.

The locked engagement between the inner and outer sheaths could then be released by rotating the recess 126 downwardly as viewed in FIGS. 2 and 7. Such rotation would cause one edge surface 128 of the recess 126 to ride over the flexible tab 122 causing it to flex inwardly and out of engagement with the recess 126. In this manner, the outer sheath 104 could then be moved to an extended position for shielding the needle. A fully extended position (not otherwise shown) of the outer sheath 104 corresponds generally to engagement or register of the recess 126 with the other projection or tab 124. Thus, when the tab 124 is engaged within the recess 126, the outer sheath 104 is locked in an extended position to assure protection for the needle 56.

Here again, the locking engagement between the inner and outer sheaths 102 and 104 may be selectively released by rotating the outer sheath 104 so that the recess 126 moves upwardly as viewed in FIGS. 2 and 7. Upon such movement of the outer sheath 104, an opposite edge surface 130 tends to ride over the tab 124 flexing it inwardly (see FIG. 6) in order to disengage the tab 124 from the recess 126.

Relative alignment between the locking means including the projections 122, 124 and the recess 126 are provided by additional guide means also formed on both of the inner and outer cylindrical sheaths while being arranged for operative interaction in generally the same manner as described above for the locking means.

The guide means include axially extending ridges 132 and 134 formed on the inner cylindrical sheath 102 on opposite circumferential sides of the tabs 122, 124. The ridges 132 and 134 include end portions 136 and 138 formed adjacent the second tab 124 and extending toward each other to form a generally central opening 140.

Referring also to FIGS. 7 and 8, a guide lug 142 projects radially inwardly from the outer cylindrical sheath 104. With the outer sheath 104 positioned over the inner sheath 102 in the manner illustrated in FIG. 1 and in the same relative positions as illustrated in FIGS. 2 and 7, the guide lug 142 is captured between the ridges 132 and 134. The opening 140 is positioned for receiving the guide lug 142 when the outer sheath 104 is initially positioned over the inner sheath 102. With the outer sheath rotated in either direction however, the end ridge portions 136 and 138 tend to intercept the guide lug 142 during extension of the outer sheath 104 in order to prevent it from being removed from the inner sheath 102.

Projections 144 are preferably formed in circumferentially spaced apart relation adjacent the outer end of the inner cylindrical sheath 102. The projections 144 preferably extend inwardly as best seen in FIG. 1 so that they engage the barrel 52 adjacent the needle hub 58. Accordingly, the projections 144 assist in maintaining the inner cylindrical sheath 102 firmly in engagement upon the barrel 52 of the hypodermic syringe 50. The projections 144 also allow for slight difference or variations in syringe barrels as might occur from one needle device to another.

It is also to be noted that the reduced diameter flange 116 on the lower end of the outer sheath 104, as viewed in FIG. 1, is also adapted for receiving a solid cap 118B. Particularly when the outer sheath is extended and preferably after use of the needle, the solid cap 118B can then be placed on the end of the extended outer sheath 104 in order to completely enclose the needle 56.

The double sheath assembly 100 of FIGS. 1–10 is intended to provide means for permitting the outer sheath 104 to be telescoped outwardly to an extended position enclosing the hypodermic needle 56, particularly after use of the needle, in order to provide maximum safety for the user of the device and hypodermic needle as well as other health care professionals and workers. Accordingly, the protective device 100 is contemplated for eliminating or greatly reducing the possibility of contact with used needles particularly in the case of contagious diseases and the like.

It is particularly important to note that the shield assembly 100 can also be used as a separate functioning unit, separate from the hypodermic syringe 50, for example, without altering or redesigning the existing syringe. The shield assembly 100 can also be used differently in different applications. For example, with the outer sheath being extended over the needle after use of the needle, it is normally locked in its extended position as described above. The terminal end of the outer sheath can then be capped with a solid cap such as that indicated at 118B and the syringe 50 and shield assembly 100 disposed of together in the usual manner.

Alternatively, the shield assembly 100 may be employed as a recapping device using a standard needle cap indicated at 62. As an alternate method of use, the needle cap may be again positioned over the needle 56 after use of the needle to facilitate disposal of the hypodermic syringe 50 alone with protection for the used needle. In that case, the shield assembly 100 may be removed from the syringe and re-sterilized, for example, to permit its reuse with another syringe.

The advantages referred to above are made more apparent in the following brief description summarizing operation of the shield assembly 100.

Initially, the shield assembly 100 is positioned on a syringe such as that indicated at 50 in FIG. 1. An existing needle cap 62 may initially remain in place upon the syringe with an open receptor cap of the type indicated at 118A being employed for retaining the needle cap in place. Three methods of using the shield assembly were described above. Here, the receptor cap 118A is only used to retain the conventional needle cap when the outer sheath is retracted.

As noted above, the receptor cap is used only to recap the needle and is placed on the outer sheath after the outer sheath is extended and locked in place. The original cap is placed into the receptor cap where it is retained so that when the outer sheath is retracted, the needle cap is brought into apposition to the needle hub (its original position). However, as noted, it would then be necessary to manually and frictionally attach and secure the needle cap to the needle hub. The receptor cap could remain in place but would serve no particular purpose in retaining the needle cap.

After use of the syringe 50 and particularly the needle 56, the needle cap 62 may be reinstalled preferably with the outer sheath 104 being in its retracted position illustrated in FIG. 1. In such an event, the receptor cap 118A could then again be placed upon the outer sheath 104 in order to secure the needle cap in place over the needle.

Alternatively, following use of the needle, the outer cylindrical sheath 104 may be telescoped to its extended position so that the second tab 124 engages the recess 126. With the outer sheath 104 in such a position, it may then be closed, for example, by means of the solid cap 118B in order to facilitate disposal of the syringe 50 and shield assembly 100 in combination.

Thus, whether the shield assembly 100 is disposed of with the syringe 50 or whether it is reserved for use with one or more additional syringes, the shield assembly 100 and the method of use described above tends to ensure that the needle remains protected after use and to prevent it from coming into undesirable contact either with the user's body or with others in the area.

Yet another embodiment of a shield assembly is indicated at 200 in FIGS. 11-19.

Referring to FIGS. 11-19 and particularly to FIGS. 11 and 19, the shield assembly 200, as indicated above, includes three telescoping sheaths, namely an inner cylindrical sheath indicated at 202, an intermediate cylindrical sheath indicated at 204 and an outer cylindrical sheath indicated at 206.

In the embodiment of FIGS. 11-19, similar locking and guide means are provided for interaction between adjacent pairs of the three sheaths in generally the same manner described above relative to the embodiment of FIGS. 1-10. However, because of the additional intermediate sheath, the locking means provided in the embodiment of FIGS. 11-19 is preferably operable only when the intermediate and outer sheaths 204 and 206 are generally fully extended relative to the inner sheath 202 and the intermediate sheath 204 respectively.

In connection with the shield assembly 200, it is described with reference to a hypodermic syringe 50' which is illustrated generally to include a needle hub 58' having a flange 59'. A needle or cannula 56' is attached to the needle hub 58' by means of a needle shank 57'. Accordingly, the needle device illustrated in FIG. 19, for example, is a different variation from the needle device illustrated in the embodiment of FIG. 1.

In any event, the inner cylindrical sheath 202 is configured for fitting over only an end portion of the hypodermic syringe 50'. Preferably, the inner cylindrical sheath 202 is adapted for frictional engagement with the needle hub 58' formed on the syringe barrel 52' for receiving a needle assembly such as that indicated either at 56A or 56B, for example.

Otherwise, the multiple sheaths 202-206 are intended to operate in generally a similar manner as described above for the embodiment of FIGS. 1-10. In particular, the sheaths may all be telescoped or nested in retracted relation in order to expose the needle 56' and permit normal operation of the syringe 50' without interference from the shield assembly 200. Alternatively, the sheaths can be shifted to their relatively extended positions so that at least the outer sheath 206 surrounds and shields the needle 56'.

Figure 10:
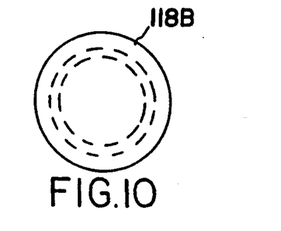

Accordingly, the shield assembly 200 of FIGS. 11-19 can also be adapted for use either with a receptor cap or solid cap of the type indicated respectively at 118A and 118B in FIGS. 1, 9 and 10. It is also to be understood that the specific caps illustrated in those figures are set forth only by way of example. The caps could have different configurations either for use with the shield assembly 200 of FIGS. 11-19, the shield assembly 100 of FIGS. 1-10 or even the shield assembly 300 described below with reference to FIGS. 20-29.

The inner cylindrical sheath 202 is formed with a single projection or tab 208 arranged generally adjacent an outer or extended end 210 of the sheath 202. Thus, the projection or tab 208 corresponds generally to the second projection or tab 124 in the embodiment of FIGS. 1-10 since it is adapted for locking in extended relation of the shield assembly.

The intermediate cylindrical sheath 204, arranged adjacent the inner cylindrical sheath 202, includes a recess or opening 212 formed generally adjacent an inner or retraction end of the intermediate sheath 204. Here again, the recess or opening 212 is of a similar configuration as the tab 208 to permit locking engagement in the same manner described above for the embodiment of FIGS. 1-10.

An additional projection or tab 216 is also formed adjacent an outer or extension end of the intermediate sheath 204. Yet another recess or opening 220 is formed adjacent an inner or retraction end 222 of the outer cylindrical sheath 206.

The two projections or tabs 208 and 216 formed on the outer ends of the inner cylindrical sheath 202 and intermediate cylindrical sheath 204 respectively preferably extend in the same circumferential direction as illustrated in FIGS. 12-15.

Guide means similar to those described in connection with the embodiment of FIGS. 1-10 are also formed jointly on the inner cylindrical sheath 202 and the intermediate cylindrical sheath 204 as well as on the intermediate cylindrical sheath 204 and the outer cylindrical sheath 206 in order to assure continued alignment of the locking means formed by the projection or tab 208 and recess or opening 212 as well as the projection or tab 216 and recess or opening 220.

In this regard, guide ridges 224 and 226 are formed on the inner cylindrical sheath 202 in generally the same manner describe above as the ridges 132 and 134 in FIGS. 1-10. The guide ridges 224 and 226 are provided with similar end portions 228 and 230 as well as an opening 232.

A guide lug 234 is arranged internally on the intermediate cylindrical sheath 204 as illustrated in FIG. 16. The guide lug 234 is contemplated for capture between the guide ridges 224 and 226 when the inner and intermediate cylindrical sheaths 202 and 204 are arranged in telescoping relation with the tab 208 in axial alignment with the recess 212.

Similar guide ridges 236 and 238 are formed on the intermediate cylindrical sheath 204 together with end portions 240 and 242 forming an opening 244.

Figure 17:
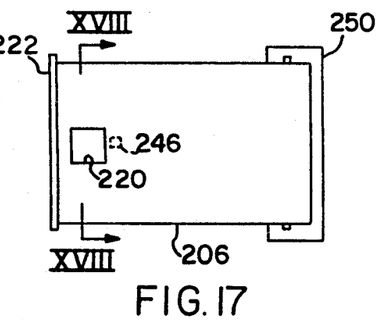
FIG. 17 is a longitudinal side view of an outer sheath in the shield assembly of FIG. 11.

A guide lug 246 is also arranged internally adjacent an inner or retraction end 248 of the outer cylindrical sheath 206 as illustrated in FIGS. 17 and 18.

The guide means described above operate in generally the same manner together with the locking means as in the embodiment of FIGS. 1-10.

Initially, the three sheaths 202-206 may be arranged in nested or telescoping relation by aligning the respective guide lugs 234 and 246 respectively with the openings 232 and 244 in the guide means.

With the three sheaths arranged in nested relation, they may then be fully retracted, for example, to the position illustrated in FIG. 19 with the needle 56' being exposed. The syringe 50' can then be used in the conventional manner so that the shield assembly 200 does not interfere with its operation.

After use of the hypodermic syringe and particularly the needle 56', the intermediate and outer cylindrical sheaths 204 and 206 may then be shifted into relatively extended positions as illustrated in FIG. 11. As the sheaths approach these extended positions, the projections or tabs 208 and 216 approach into register and engagement respectively with the recesses or openings indicated respectively at 212 and 220. Thus, the shield assembly 200 can be locked in its fully extended position to protect or shield the needle 56'. With the sheaths in their extended positions following use of the needle 56', a solid cap 250 may then be positioned on the outer or extended end of the outer cylindrical sheath 206 in generally the same manner described above relative to the embodiment of FIGS. 1-10.

Otherwise, the shield assembly 200 of FIGS. 11-19 is capable of alternative methods of use in generally the same manner described above for the embodiment of FIGS. 1-10. These alternate uses include the shield assembly 200 being adapted for use with an existing syringe 50' while not requiring any structural modification of the syringe. Furthermore, the shield assembly 200 may either be sterilized and reused or disposed of in combination with a single syringe.

As was also noted above, a third embodiment of a shield assembly constructed according to the present invention is generally indicated at 300 in FIGS. 20-29. The shield assembly 300 also includes three telescoping sheaths comprising an inner cylindrical sheath 302, an intermediate cylindrical sheath 304 and an outer cylindrical sheath 306.

Initially, it is noted that the shield assembly 300 is similarly adapted for mounting on an end portion of a syringe 50' in generally the same manner as described above for the embodiment of FIGS. 11-19.

Accordingly, the inner cylindrical sheath 302 is similarly adapted for frictional engagement with the needle hub 58' of the hypodermic syringe 50'.

The shield assembly 300 also includes locking means for securing the three sheaths 302-306 in relatively fully extended relation. Further, the respective sheaths in the shield assembly 300 of FIGS. 20-29 include spiral or helical tracks for permitting relative rotation between adjacent sheaths into either retracted or extended relation. These features of the shield assembly 300 are described in greater detail below.

Initially, the inner cylindrical sheath 302 is formed with projections 308 in the form of a spiral ring extending substantially along the entire outer cylindrical surface thereof. The inner cylindrical sheath 302 also has two axially spaced apart circumferential projecting rings 310 and 312 arranged generally adjacent an outer or extension end 314 of the inner cylindrical sheath 302. The rings 310 and 312 are also formed with four relatively offset openings 316, 318, 320 and 322.

Four projecting lugs 324-330 are internally formed on the intermediate cylindrical sheath 304 adjacent its inner or retraction end 332. The lugs 324-330 are uniformly spaced apart about the circumference of the intermediate sheath 304 while being in axial alignment with each other.

The spacings between the openings 316-322 are selected so that the lugs 324-330 can pass through the openings in the outer ring 312, the intermediate cylindrical sheath 304 then being rotated slightly relative to the inner cylindrical sheath 302 so that the lugs 324-330 register with and can pass through the openings in the other ring 310.

The circumferential spacing between adjacent pairs of the lugs 324-330 is further selected so that any two adjacent lugs are capable of capturing the spiral rings 308 therebetween. For example, the four lugs 324-330 are best illustrated on the developed surface view of the inner cylindrical sheath 302 in FIG. 27. As best seen in that figure, the spiral ring or track 308 is then captured between two of the lugs indicated respectively at 326 and 328. Thereafter, relative rotation of the inner and intermediate cylindrical sheaths 302 and 304 causes relative extension or retraction between the sheaths depending upon the relative direction of rotation.

Two detent surfaces 334 are also formed in the spiral track 308. As the intermediate cylindrical sheath is being rotated into extension relative to the inner cylindrical sheath 302, two engaging lugs, for example those indicated at 326 and 328, are engaged by the detent surface 334 in order to produce a locking effect similar to the locking means described for the embodiments of FIGS. 1-10 and 11-19 respectively.

A similar spiral track projection 336 is also formed on an external surface of the intermediate cylindrical sheath 304. Similar projecting rings 338 and 340 are also formed on the intermediate cylindrical sheath 304 adjacent its outer or extension end 332.

Four inwardly projecting lugs 344-350 are also formed adjacent an inner or retraction end 352 of the outer cylindrical sheath 306. The features described immediately above on the intermediate cylindrical sheath 304 and the outer cylindrical sheath 306 conform to the corresponding features described in combination above on the inner cylindrical sheath 302 and the intermediate cylindrical sheath 304.

Here again, the shield assembly 300 of FIGS. 20-29 is capable of the same alternate methods of use described above particularly with reference to the embodiment of FIGS. 1-10 and also generally referred to in connection with the embodiment of FIGS. 11-19.

A method of use for the shield assembly 300 of FIGS. 20-29 is briefly described below in order to assure its operation.

Figures 20, 21, 22, 23, 24, 25, 26, 27, 28, 29:
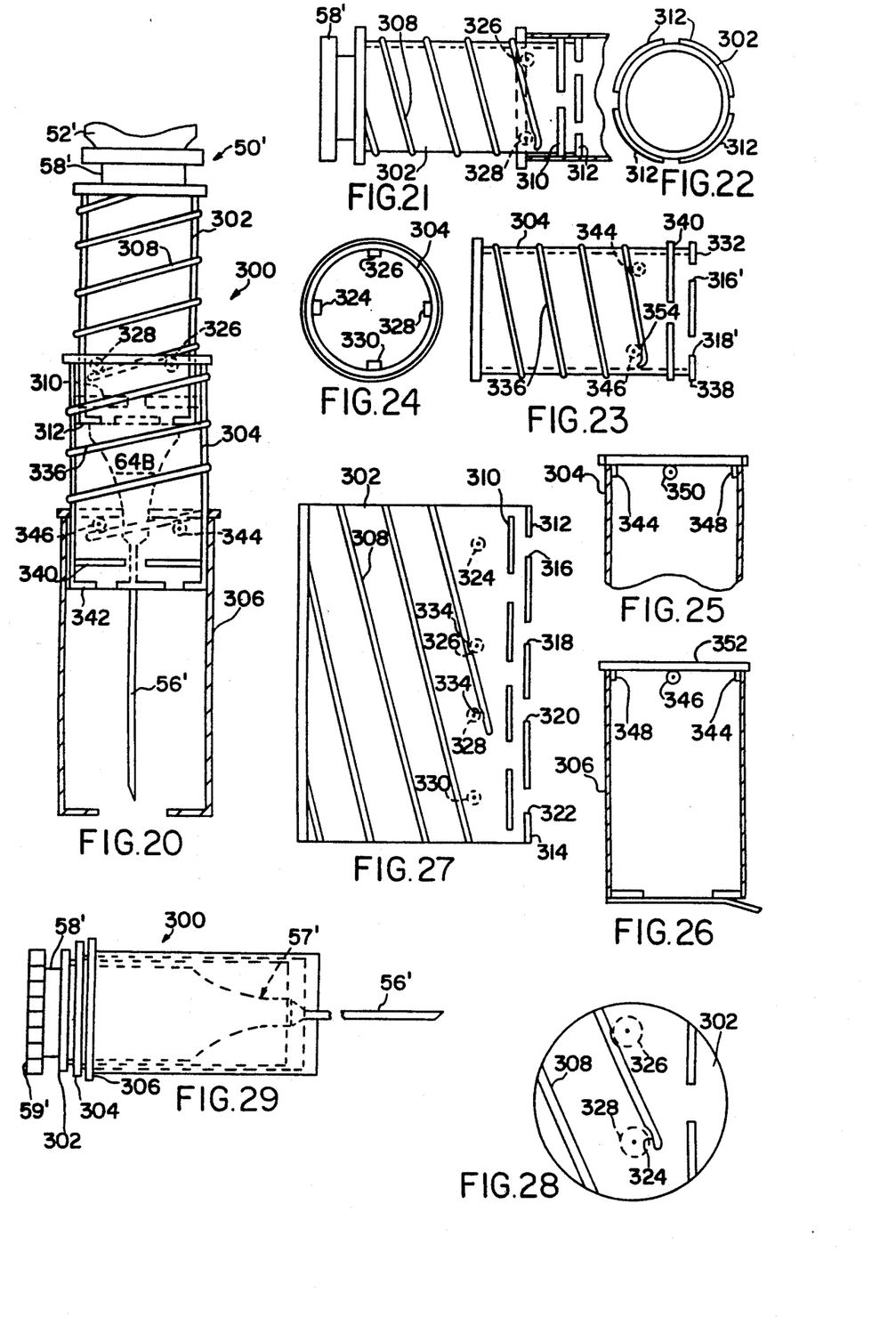
FIG. 20 is a longitudinal side view, with parts in section, of an third embodiment of a shield assembly constructed according to the present invention for use on a hypodermic syringe and the like, telescoping sheaths in the shield assembly of FIG. 20 being illustrated in generally fully extended relation.
FIG. 21 is a longitudinal side view of an inner sheath in the shield assembly of FIG. 20.
FIG. 22 is an end view of the inner sheath of FIG. 1 taken from its right end as viewed in FIG. 21.
FIG. 23 is a longitudinal side view of an intermediate sheath in the shield assembly of FIG. 20.
FIG. 24 is an end view of the intermediate sheath of FIG. 23 taken from the left end of the outer sheath as illustrated in FIG. 23.
FIG. 25 is a fragmentary and axially sectioned longitudinal side view of the intermediate sheath in order to better illustrate lugs internally formed on the intermediate sheath for engagement with the spiral track on the inner sheath of FIG. 21.
FIG. 26 is a longitudinal side view, with parts in section, of an outer sheath from the shield assembly of FIG. 20.
FIG. 27 is a developed view of the outer circumferential surface of the inner sheath also illustrated in FIG. 21, lugs from the intermediate sheath of FIGS. 23 and 24 being represented in phantom in order to illustrate their interaction with a spiral track on the inner sheath.
FIG. 28 is an enlarged fragmentary view of a portion of the developed surface of the inner sheath while also including the phantom representation of the lugs from the intermediate sheath in order to better illustrate interaction between the adjacent sheaths.
FIG. 29 is a side view generally similar to FIG. 20 but with the sheaths of the shield assembly being generally fully retracted in order to expose the hypodermic needle.

Initially, the three sheaths 302-306 are assembled in nested and preferably retracted relation as illustrated in FIG. 29. Here again, the shield assembly 300 can be used either with a needle cap of the type described in connection with the embodiment of FIGS. 1-10 and/or with different types of needle assemblies.

Prior to use, any such needle cap is removed if present so that the needle 56' is exposed by the retracted sheaths 302-306.

After use of the syringe and needle as described above, the sheaths 302-306 are extended by relative rotation along the spiral tracks 308 and 336 so that certain of the lugs 324-330 and 344-350 engage the detents 334 and 354 in order to generally lock the shield assembly 300 in its extended position.

Here again, the outer cylindrical sheath 306 may then be closed, for example with a solid cap (not shown), in order to simultaneously dispose of the syringe 50' and shield assembly 300. Alternatively the shield assembly 300 can be removed from the syringe 50', the needle 56' on the syringe preferably being shielded by a needle cap or the like for disposal of the syringe.

The shield assembly 300 may then be sterilized and reused, for example, in generally the same manner as described for the other embodiments.

As was also noted above, a fourth embodiment of a shield assembly constructed according to the present invention is generally indicated at 400 in FIGS. 30–36 and includes an inner cylindrical sheath 402, an intermediate cylindrical sheath 404 and an outer cylindrical sheath 406 arranged in telescoping relation with each other.

The shield assembly 400 is also preferably adapted for mounting on an end portion of a syringe 50' in generally the same manner as described above for the embodiments of FIGS. 11–19 and FIGS. 20–29. Accordingly, the inner cylindrical sheath 402 is preferably adapted for frictional engagement with the needle hub 58' of the hypodermic syringe 50'.

As also noted above, the shield assembly 400 includes the first spring 408 arranged for interaction between the inner and intermediate sheaths 402 and 404 for urging them into relatively extended relation. Similarly, the second spring 410 is arranged for interaction between the intermediate and outer cylindrical sheaths 404 and 406 for urging them into relatively extended relation.

Figure 31:
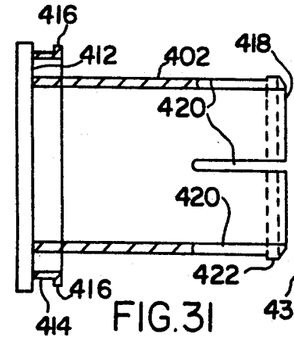
FIG. 31 is a longitudinal side view of an inner sheath in the shield assembly of FIG. 30.
Figures 32, 33:
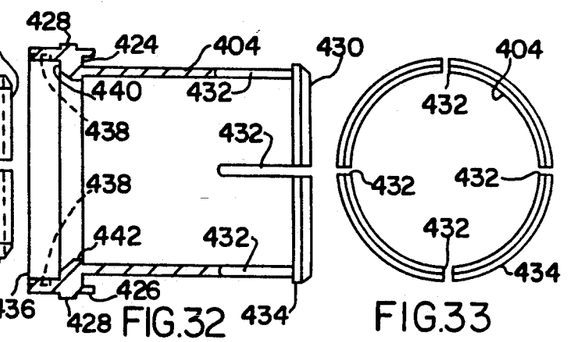
FIG. 32 is a longitudinal side view of an intermediate sheath in the shield assembly of FIG. 30.
FIG. 33 is an end view of the intermediate sheath taken from the right end of FIG. 32.
Figure 34:
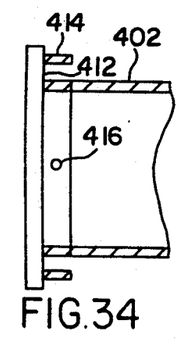
FIG. 34 is a fully sectioned view of a fragmentary portion of the inner sheath also illustrated in FIG. 31.
Figure 35:
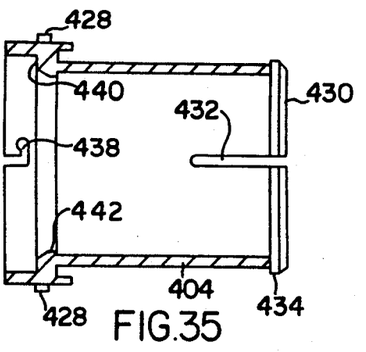
FIG. 35 is a fully sectioned view of the intermediate sheath also illustrated in FIGS. 32 and 33, FIGS. 34 and 35 illustrating in combination locking means for securing the inner and intermediate sheaths together.
Figure 36:
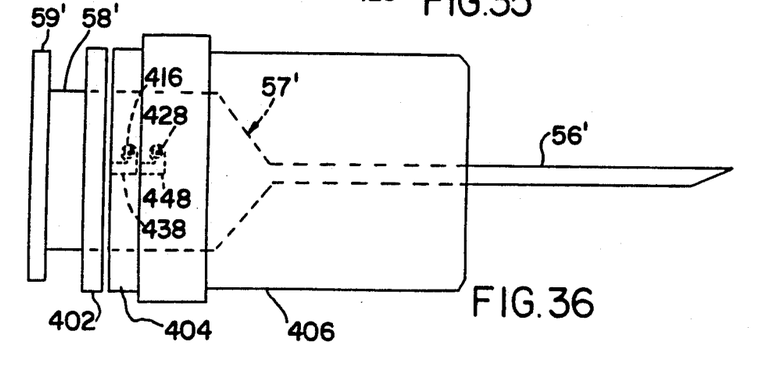
FIG. 36 is a pictorial side view of the shield assembly of FIG. 30 with the inner, intermediate and outer sheaths secured in retracted relation upon the syringe for exposing the needle and permitting normal operation of the syringe.

Referring also to FIG. 31, the inner cylindrical sheath 402 is formed with an annular recess 412 for receiving one end of the spring 408. An annular flange 414 forms the recess 412 and also supports diametrically spaced apart hooks or projections 416 for a purpose to be described in greater detail below. The outer end 418 of the inner cylindrical sheath 402 is formed with circumferentially spaced apart and axially extending slots 420 also for a purpose to be described in greater detail below. The inner cylindrical sheath 402 also has a radially outwardly projecting annular ridge 422 formed at its outer end 418.

The intermediate cylindrical sheath 404 is also formed with an annular recess 424, an annular flange 426, hooks or projections 428, an outer end 430 with slots 432 and an annular ridge 434 formed in generally the same manner as described above for the elements 412–422 on the inner cylindrical sheath 402.

Figure 30:
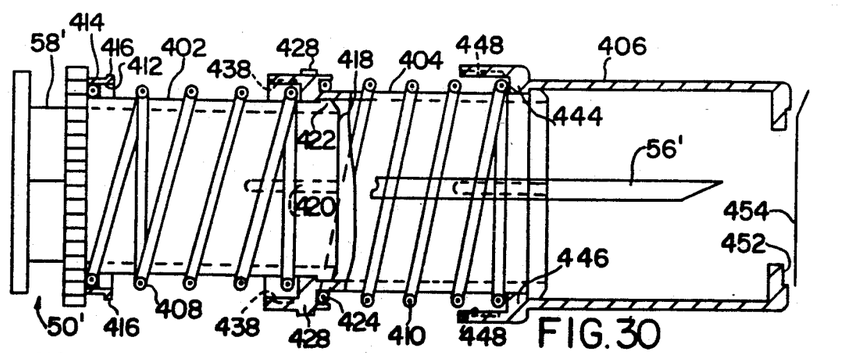
FIG. 30 is a longitudinal side view, with parts in section, of a fourth embodiment of a shield assembly constructed according to the present invention for use on a hypodermic syringe or the like, telescoping sheaths of the shield assembly being illustrated in a relatively extended condition.

In addition, an inner end 436 of the sheath 404 is formed with locking recesses 438 diametrically positioned and facing radially inwardly for locking engagement with the hooks 416. The inner end 436 of the intermediate sheath 404 also forms an annular recess 440 arranged in opposed relation with the annular recess 412 for capturing or retaining the first spring 408 for interaction between the inner and intermediate sheaths 402 and 404. Referring also to FIG. 30, it may be seen that the annular recess 440 functions in combination with the inner cylindrical sheath 402 for retaining the first spring in place.

The intermediate cylindrical sheath 404 also has a radially inwardly facing annular ridge 442 formed generally adjacent its inner end 436. During assembly, when the inner cylindrical sheath 402 of FIG. 31 is placed in telescoping relation with the intermediate sheath 404, the slots 420 permits the outer end 418 of the sheath 402 to slightly collapse so that the radially outwardly facing annular ridge 422 on the inner sheath 402 may pass the radially inwardly facing annular ridge 442 on the intermediate sheath 404. After the sheaths 402 and 404 are in telescoping relation, the ridges 422 and 442 interact and tend to prevent the intermediate sheath 404 from accidentally being disengaged from the inner sheath 402.

Referring again to FIG. 30, the outer cylindrical sheath 406 is formed with an annular recess 444 similar to the recess 440 on the intermediate sheath 404. Similarly, the outer sheath 406 is formed with a radially inwardly facing annular ridge 446 generally similar to the annular ridge 442 on the intermediate sheath. The outer sheath 406 also has locking recesses 448 similar to the locking recesses 438 on the intermediate sheath. The locking recesses 448 are adapted for locking engagement with the hooks or projections 428 on the intermediate sheath in the same manner described above for the hooks 416 and locking recesses 438 respectively arranged on the inner and intermediate sheaths. An outer end 450 of the outer sheath 406 is formed with a recess 452 for receiving a cap or closure 454 if desired to completely enclose the needle 56'. With the shield assembly 400 arranged upon the needle hub 58' as illustrated in FIG. 30, the three sheaths 402, 404 and 406 are urged into their relatively extended positions as illustrated by the spring 408 and 410. The cap 454 may then be positioned on the outer cylindrical sheath 406 as noted above for completely enclosing the needle 56'.

In order to permit normal operation of the syringe 50', with the needle 56' being exposed, the intermediate sheath 404 is retracted against the inner cylindrical sheath 402 and slightly rotated in order to engage the hooks 416 with the locking recesses 438. Similarly, the outer cylindrical sheath 406 is retracted against the spring 410 into nested relation with the intermediate sheath 404 and slightly rotated in order to lock the hooks 428 into engagement with the locking recesses 448. Accordingly, the three sheaths may be retained in the retracted position illustrated in FIG. 36 for permitting normal operation of the syringe with the needle 56' exposed. After such use, the intermediate and outer cylindrical sheaths may be slightly rotated in order to release the hooks 416 and 428 whereupon the shield assembly 400 is permitted to return to its extended position under the influence of the springs 408 and 410 as illustrated in FIG. 230. With the intermediate and outer sheaths 404 and 406 being extended under spring pressure, the shield assembly can be used for injection with the outer sheath first contacting and compressing the tissue (not shown) prior to the needle entering into the tissue and injection. This configuration causes the needle to be automatically covered after injection when the needle is removed from the tissue. The syringe and needle and shield assembly could be discarded immediately after use without capping. Those components could also be reused either individually or in combination as described above.

As was also noted above, a fifth embodiment of a shield assembly constructed according to the present invention is generally indicated at 500 in FIGS. 37–42. As noted above, the shield assembly 500 includes an inner cylindrical sheath 502 formed with an inner portion 502A and an outer portion 502B interconnected by a flexible hinge 506. The outer cylindrical sheath 504 is arranged in telescoping relation about the outer portion 502B and is movable into engagement with the other portion 502A as described in greater detail below.

The shield assembly 500 is also preferably adapted for mounting on an end portion of a syringe 50' in generally the same manner described above for the embodiments of FIGS. 11-19 and 30-36. Accordingly, the inner cylindrical sheath 502 is preferably adapted for frictional engagement with the needle hub 58' of the hypodermic syringe 50'.

A shoulder 508 is formed on an outer end 510 of the sheath 504 by a knurled annular projection 512 facilitating manipulation of the sheath 504. The shoulder 508 is adapted for engagement with a stop 514 at the extended end of the inner cylindrical sheath portion 502B. The inner cylindrical sheath portion 502B is formed with a radially inwardly facing slot 522 for permitting passage of the stop 514 during initial assembly of the shield assembly 500.

Figures 38, 39, 40, 41, 42:
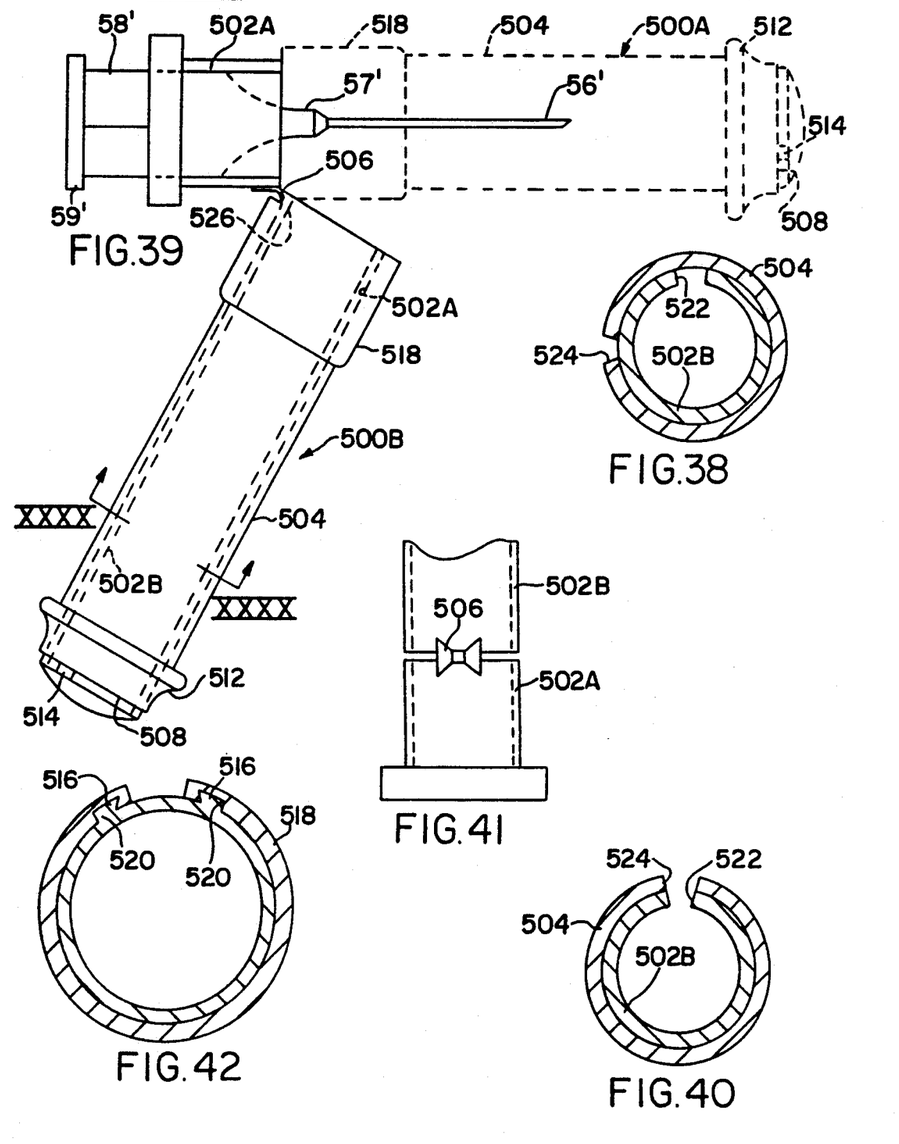
FIG. 38 is a view taken along section line XXXVIII—XXXVIII of FIG. 37.
FIG. 39 is a side view of the shield assembly similar to FIG. 37 but with a portion of the shield assembly in a hinged position to expose a needle of the syringe, the hinged portion of the shield assembly also being illustrated in phantom prior to movement into its hinged position.
FIG. 40 is a view taken along section line XXXX—XXXX of FIG. 39.
FIG. 41 is a fragmentary view of two portions of the shield assembly and an interconnecting hinge means.
FIG. 42 is a view taken along section line XXXXII—XXXXII in FIG. 37.

The base portion 502A of the inner cylindrical sheath is formed with axially extending ridges 516 as best illustrated in FIG. 42. An enlarged end portion 518 of the outer cylindrical sheath 504 is formed with mating recesses 520 for receiving the ridges 516 when the enlarged end portion 518 of the outer cylindrical sheath 504 is moved into telescoping relation with the inner cylindrical sheath portion 502A.

Referring also to FIGS. 38 and 40, the inner cylindrical sheath portion 502B is formed with a slot 522 extending in axial alignment substantially along the entire length of the inner cylindrical sheath 502B. A similar slot 524 is formed in the outer cylindrical sheath 504 as illustrated in both of FIGS. 37 and 38.

With the outer cylindrical sheath 504 rotated so that its slot 524 is approximately 90° out of alignment with the slot 522, the ridges 516 are in alignment with the recesses 520 (see FIG. 42). The outer cylindrical sheath 504 is retained in this rotated position when it is retracted onto the inner cylindrical sheath base portion 502A. Accordingly, the ridges 516 engage the recesses 520 for locking the shield assembly 500 in a position enclosing or shielding the needle 56'. This shielded or protected position of the shield assembly is indicated at 500A in FIG. 37 and in phantom in FIG. 39.

Figure 37:
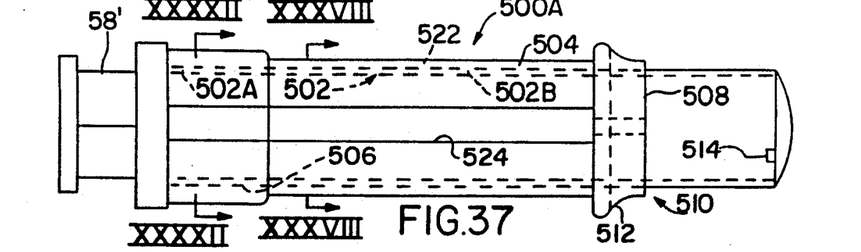
FIG. 37 is a longitudinal side view of a fifth embodiment of a shield assembly constructed according to the present invention for use on a hypodermic syringe and the like, telescoping sheaths in the shield assembly being illustrated in a position for shielding a needle or needle assembly of the syringe.

In order to permit normal operation of the syringe 50', the outer cylindrical sheath 504 is initially moved outwardly or rightwardly as illustrated in FIG. 37 until its shoulder 508 engages the stop 514. The outer cylindrical sheath 504 can then be rotated to the position illustrated in FIG. 40 so that the slots 522 and 524 are in register or alignment with each other. At the same time, the hinge 506 is exposed so that the inner cylindrical sheath portion 502B and the outer cylindrical sheath 504 can then be hinged into the retracted position indicated at 500B in FIG. 39. The hinge 506 is preferably of a type tending to retain the shield assembly 500 with the inner cylindrical sheath portion 502B and outer cylindrical sheath 504 in either the shielded position indicated at 500A in FIG. 37 or in the retracted or hinged position indicated at 500B in FIG. 39.

After use of the syringe, the hinged portion 500B can then be moved back to the position 500A with the aligned slots 522 and 524 permitting relative passage of the needle 56'. With the shield portion 500B returned to its shielded position 500A, the outer cylindrical sheath 504 may then be rotated back to the position illustrated in FIG. 38 so that the slots 522 and 524 are out of engagement with each other. At the same time, the ridges 516 are again brought into alignment with the mating recesses 520 so that the outer cylindrical sheath 504 may be retracted over the base portion 502A of the inner cylindrical sheath. If desired, the enlarged end portion 518 of the outer cylindrical sheath 504 may be formed with a circumferential recess 526 for mating with the hinge 506 when the outer cylindrical sheath 504 is extended outwardly against the stop 514. The circumferential length of the recess 526 may be selected if desired for limiting relative rotation of the outer cylindrical sheath 504 either to assure alignment of the slots 522 and 524 or, at its other extremity, to ensure alignment of the ridges 516 with the recesses 520.

Accordingly, there have been described five embodiments of a shield assembly suitable for use with a hypodermic syringe, an intravenous device or or other needle assembly. Various modifications and additions besides those specifically described above will be apparent from the preceding description. Accordingly, the scope of the present invention is defined only by the following appended claims which are further exemplary of the invention.

What is claimed is:

1. A shield assembly for a separate syringe having a barrel portion with plunger means at one end and means at its other end for connection to a needle assembly, comprising an inner cylindrical sheath, an outer cylindrical sheath, one of the inner and outer cylindrical sheaths being configured for engagement with the separate syringe to selectively permit normal operation of the syringe, the other of the inner and outer cylindrical sheaths being mounted on the one cylindrical sheath for movement between a first extended position shielding the needle assembly and a second retracted position exposing the needle assembly for normal operation of the syringe, and locking means for securing the other cylindrical sheath in a selected position on the one cylindrical sheath, the locking means comprising a projecting tab and recess means respectively arranged on the two sheaths for relative engagement with the sheaths in extended relation, the projecting tab extending tangentially from its sheath for engagement with the recess means and for release by relative rotation of the inner and outer cylindrical sheaths to permit relative retraction and exposure of the needle assembly.

2. The shield assembly of claim 1 wherein the inner cylindrical sheath is configured for receiving and engaging the syringe barrel.

3. The shield assembly of claim 2 further comprising snap-fit means for engaging the inner cylindrical sheath with a portion of the syringe barrel.

4. The shield assembly of claim 1, further comprising guide means formed on the inner and outer cylindrical sheaths and arranged for operative interaction to maintain the projecting means and recess means of the locking means in alignment with each other.

5. The shield assembly of claim 4 wherein the inner cylindrical sheath is configured for engagement with the syringe barrel, the outer cylindrical sheath being movable into retracted nesting relation with the inner cylindrical sheath or into its extended position.

6. The shield assembly of claim 5 further comprising snap-fit means on the inner cylindrical shield for engaging a portion of the syringe barrel.

7. The shield assembly of claim 4 wherein the locking means comprises similar means effective to lock the outer cylindrical sheath in its retracted position.

8. The shield assembly of claim 23 further comprising two resilient cutout tabs tangentially extending in opposite circumferential directions on the inner cylindrical sheath, the guide means including projecting means on the inner and outer cylindrical sheaths permitting relative rotation of the inner and outer cylindrical sheaths for releasing either of the resilient tabs from engagement with the opening.

9. The shield assembly of claim 1 further comprising an additional cylindrical sheath arranged in retractable and extendable relation on the other cylindrical sheath and a similar locking means for securing the additional sheath on the other sheath.

10. The shield assembly of claim wherein the locking means comprises similar means effective to lock the outer cylindrical sheath in its retracted position.

11. The shield assembly of claim 7 wherein the locking means comprises a single recess and two projecting tabs respectively on the two sheaths, the two projecting tabs being arranged in opposed tangential relation.

12. The shield assembly of claim 10 wherein the locking means comprises a single recess and two projecting tabs respectively on the two sheaths, the two projecting tabs being arranged in opposed tangential relation.

13. The shield assembly of claim 4 further comprising an additional cylindrical sheath arranged in retractable and extendable relation on the other cylindrical sheath and a similar locking means for securing the additional sheath on the other sheath.

* * * * *

UNITED STATES PATENT AND TRADEMARK OFFICE
CERTIFICATE OF CORRECTION

PATENT NO. : 5,242,416

DATED : September 7, 1993

INVENTOR(S) : Clifford L. Hutson

It is certified that error appears in the above-identified patent and that said Letters Patent is hereby corrected as shown below:

In column 1, line 10, "Needles" should be —Needle—.

In column 12, line 52, "describe" should be —described—.

In column 16, line 29, "spring" should be —springs—.

In column 16, line 49, "230" should be —30—.

In column 18, line 14, the second occurrence of "or" should be deleted.

In column 19, line 4, "23" should be —6—.

In column 20, line 1, —9— should be inserted after "claim".

Signed and Sealed this

Fifth Day of April, 1994

Attest:

BRUCE LEHMAN

*Attesting Officer*   *Commissioner of Patents and Trademarks*